United States Patent [19]

Ito

[11] 4,425,112
[45] Jan. 10, 1984

[54] FLOW-THROUGH CENTRIFUGE

[75] Inventor: Yoichiro Ito, Bethesda, Md.

[73] Assignee: The United States of America as represented by the Department of Health and Human Services, Washington, D.C.

[21] Appl. No.: 661,114

[22] Filed: Feb. 25, 1976

[51] Int. Cl.³ .............................................. B04B 9/00
[52] U.S. Cl. ...................................... 494/18; 494/45; 494/84
[58] Field of Search ..................... 233/24, 23 R, 23 A, 233/25, 26, 7; 350/7; 494/18, 45, 84

[56] References Cited

U.S. PATENT DOCUMENTS

| | | | |
|---|---|---|---|
| 3,586,413 | 6/1971 | Adams | 350/7 |
| 3,672,564 | 6/1972 | Schlutz et al. | 233/26 |
| 3,724,747 | 4/1973 | Unger et al. | 233/26 |
| 3,747,843 | 7/1973 | Joyce | 233/1 D |
| 3,775,309 | 11/1973 | Ito et al. | 233/25 UX |
| 3,885,735 | 5/1975 | Westberg | 233/25 |
| 3,986,442 | 10/1976 | Khoja | 74/797 |

OTHER PUBLICATIONS

Science Publication "New Flow-Through Centrifuge Without Rotating Seals Applied to Plasmapheresis", Yoichiro Ito et al., vol. 189, No. 4207, Sep. 19, 1975, pp. 999, 1000.

Primary Examiner—George H. Krizmanich
Attorney, Agent, or Firm—Joseph A. Hill; Thomas J. Byrnes; William O. Geny

[57] ABSTRACT

A flow-through centrifuge free of rotating seals. The centrifuge includes a frame having three spaced apart horizontal plates which carry a central bowl, a countershaft and a tube-supporting hollow shaft. A motor is arranged to drive the frame at an angular velocity of $\omega$. The countershaft is driven by a stationary pulley on the motor and drives the bowl at an angular velocity of $2\omega$. The motion of the countershaft is also transferred to the tube-supporting hollow shaft by a pulley coupling having a ratio which effects rotation of the hollow shaft, with respect to the frame, at an angular velocity of $-\omega$.

13 Claims, 6 Drawing Figures

FLOW-THROUGH CENTRIFUGE

FIELD OF THE INVENTION

This invention relates to flow-through centrifuges free of rotating seals. The present invention relates, more particularly, to flow-through centrifuges which provide continuous transfer of material into and out from a centrifuge bowl via tubes which are directly connected to the bowl from outside of the centrifuge without the use of rotating seals.

BACKGROUND OF THE INVENTION

Conventional flow-through centrifuges utilize rotating seals which can become a source of leaks between the inflow and the outflow lines. The rotating seals represent a weak point in the machinery in terms of the performance life time, complexity and fragility of its parts and the necessity for a continuous and comparable degree of lubrication, all shortcomings of prior art centrifuges of flow-through type. These shortcomings are distinct disadvantages no matter what materials are to be centrifuged on a flow-through basis.

When these continuous-flow centrifuges are adapted for an on-line blood separation, as applied to the collection of blood cells, rotating seals become critical in terms of platelet injury, red cell hemolysis, and obstruction of the channels by aggregates and impaired lubrication of the rotating seals.

SUMMARY OF THE INVENTION

It is an object of the present invention to provide a flow-through centrifuge which does not require any rotating seals.

It is another object of the present invention to provide a flow-through centrifuge which avoids the possibility of leaks between inflow and outflow lines.

It is a further object of the present invention to provide a flow-through centrifuge which has a long performance life time.

It is an additional object of the present invention to provide a flow-through centrifuge which is both simple and robust.

It is yet another object to provide a flow-through centrifuge which can be used for on-line blood separation without injury to platelets and without red cell hemolysis.

The foregoing objects, as well as others which are to become clear from the text below, are achieved in accordance with the present invention by providing a flow-through centrifuge which includes a centrifuge bowl operatively arranged to rotate about a central axis at an angular velocity of $2\omega$. A bundle of tubes, constituting at least one inflow line and at least one outflow line, is connected at one end to the bowl and is tightly supported at its other end. The bundle of tubes is formed in a partial loop radially displaced from the central axis. The partial loop is operatively arranged to rotate about the central axis at an angular velocity of $\omega$. The bundle of tubes remains free of twisting by being counterrotated about its own axis at $-\omega$.

DETAILED DESCRIPTION OF PREFERRED EMBODIMENTS

Figure 1:
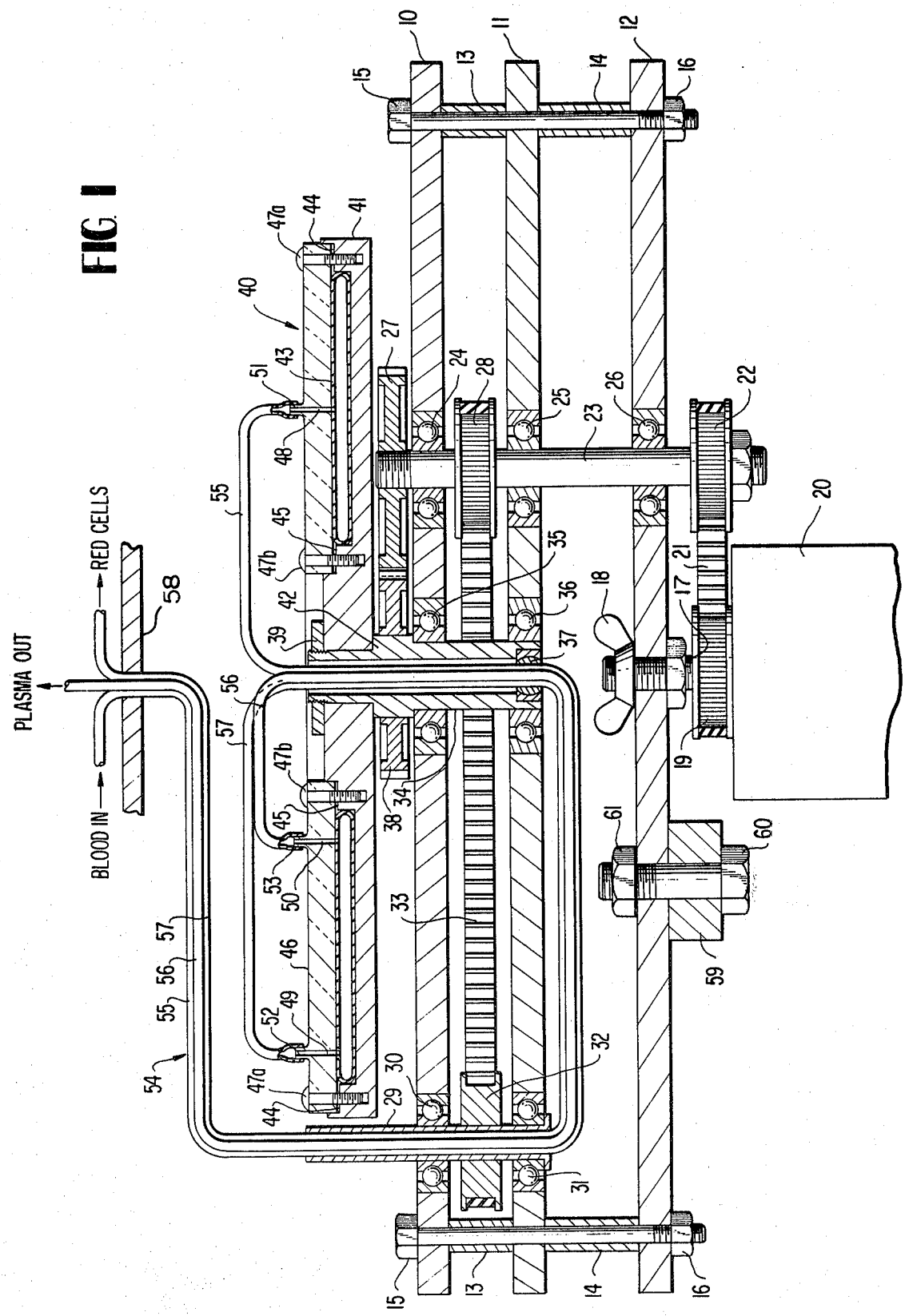
FIG. 1 is an elevational view of a flow-through centrifuge according to a first embodiment of the present invention, its bowl and a number of other parts being shown in cross section for purpose of clarity.
Figure 2:
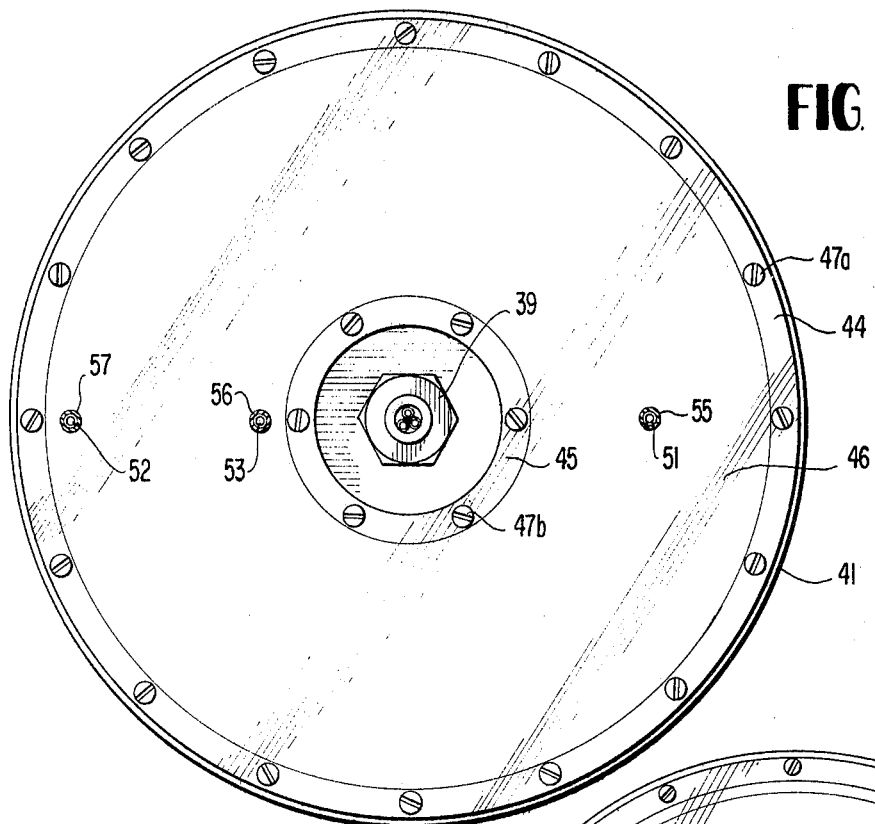
FIG. 2 is a top plan view of the centrifuge bowl forming part of the centrifuge of FIG. 1.

As illustrated in FIGS. 1 and 2, an illustrative embodiment of a flow-through centrifuge according to the present invention, includes a frame composed of three spaced-apart, horizontal, circular plates 10–12. Each of the plates 10–12 is provided with a plurality of apertures which extend through the plate near its periphery. Corresponding apertures in each of the plates 10–12 are axially aligned with one another. A plurality of tubular spacers 13 are positioned between the plates 10 and 11 and a further plurality of tubular spacers 14 are positioned between the plates 11 and 12 in alignment with the aforementioned apertures, only two of the tubular spacers 13 and two of the tubular spacers 14 being visible in FIG. 1. Bolts 15 extend through the respective axially aligned apertures in the plates 10–12 and the corresponding tubular spacers 13 and 14, each bolt 15 being held in place by a corresponding respective nut 16. The rigidly connected plates 10–12 are driven by a motor shaft 17 which is fixed to the center of the lowest plate 12 by conventional means, shown as a wing nut 18. A stationary toothed pulley 19 is mounted on the motor housing 20, the stationary pulley 19 being connected, via a toothed belt 21 to a toothed pulley 22 which is fixed to the lower end of a countershaft 23. The countershaft 23 extends through apertures in the plates 10–12 within which respective ball bearings 24–26 have been fixedly positioned. A gear 27 is fixedly connected to the upper end of the countershaft 23 and a toothed pulley 28 is fixedly connected to the countershaft 23 between the plates 10 and 11.

As shown to the left in FIG. 1, a rigid, hollow shaft 29 is positioned within further apertures provided in the respective plates 10 and 11 and operatively positioned so as to be rotatable in respective ball bearings 30 and 31 which are respectively fixed in these additional apertures in the respective plates 10 and 11. A toothed pulley 32 is fixedly connected to the hollow shaft 29 and coupled to the pulley 28 via a toothed belt 33.

A hollow shaft 34 extends through centrally positioned apertures in the plates 10 and 11, this hollow shaft 34 being positioned for rotation within ball bearings 35 and 36 which are carried respectively in the central apertures of the respective plates 10 and 11, a spherical bearing 37 being provided for supporting the lower end of the hollow shaft 34. A gear 38 is fixed to the hollow shaft 34 and meshed with the gear 27, the gears 38 and 27 having a 1:1 ratio. The upper end of the hollow shaft 34 is threaded to receive a ring nut 39.

As illustrated in FIGS. 1 and 2, a centrifuge bowl 40 according to the first embodiment of the present invention, includes a base member 41, preferably constructed of aluminum. The base member 41 has a central aperture through which the hollow shaft 34 extends, and is clamped between the ring nut 39 and a flange 42 which extends radially outward from the hollow shaft 34 above the gear 38. A donut-shaped, transparent silicon rubber bag 43 is positioned fixedly within a recess formed in the upper surface of the base member 41. The base member 41 is provided with a first shoulder 44 which extends radially outward from and adjacent to the recess within which the silicon rubber bag 43 is positioned. The base member 41 has a second shoulder 45 which extends radially inward and adjacent to the recess within which the silicon rubber bag 43 is positioned. A flat, centrally apertured, transparent, plastic lid 46, which can be advantageously made of lucite, is positioned over the recess in the base member 41. The lid 46 is held in position by a first plurality of bolts 47a and a second plurality of bolts 47b which extend through the transparent plastic lid 46 and respectively into the base member 41 beneath the respective shoulders 44 and 45, although each of the bolts 47a, 47b could extend through the base member 41 and be held by an associated nut. As illustrated, the transparent lid 46 is provided with three bores 48-50 positioned at different radial distances from the axis of rotation of the drive shaft 17. The bores 48-50 are in fluid communication with the interior of the silicon rubber bag 43, via respective apertures therein. As visible in FIG. 2, the bores 48-50 terminate not in the flat upper surface of the transparent lid 46, but rather extend through respective nipple-like protuberances 51-53 which project upwardly in the otherwise flat upper surface of the transparent lid 46.

A bundle 54 consisting of three flexible tubes 55, 56 and 57 is fixed within an opening which is coaxial with the drive shaft 17 and may be formed, for example, in a cover 58 associated with the housing of the centrifuge. The bundle 54 of tubes 55-57 extends radially outward from the axis of rotation of the drive shaft 17 to the hollow shaft 29, downwardly through the hollow shaft 29, radially inwardly from beneath the hollow shaft 34 and upwardly through the hollow shaft 34 so that each of the tubes 55-57 is positioned above the transparent lid 46. The flexible tube 55 is positioned over the nipple-like protrusion 51 on the surface of the lid 46 and communicates with the interior of the silicon rubber bag 43, via the bore 48 for the purpose of feeding blood into the bag 43. The free ends of the respective flexible tubes 57 and 56 are positioned respectively over the nipple-like protrusions 52 and 53 formed in the surface of the lid 46 so as to communicate with the interior of the silicon rubber bag 43, via respective bores 49 and 50, at different radial distances from the axis of rotation of the centrifuge as defined by the axis of rotation of the drive slaft 17. As illustrated, whole blood may be fed into the silicon rubber bag 43 via the flexible tube 55, flexible tubes 56 and 57 providing conduits for removing respectively plasma and red cells from the interior of the silicon rubber bag 43. It is to be appreciated that suitable pumps (not shown) may be provided for feeding blood into the flexible tube 55 and for pumping blood components from the flexible tubes 56 and 57.

A counterweight 59 is provided beneath the plate 12, it being held in place by a bolt 60 and an associated nut 61. The counterweight 59 is positioned radially opposite to the pulley 22 and the countershaft 23 so as to balance the frame.

It is to be appreciated that the silicon rubber bag 43 may be equipped with three internal flow lines, in lieu of its illustrated fluid communication with the bores 48-50, these internal flow lines communicating with the flexible tubes 55-57 either through the transparent lid 46 or other apertured portions of the bowl 40.

In operation, the drive shaft 17 of the drive motor drives the frame, including the horizontal plates 10-12, at a particular selected angular velocity $\omega$, for example at 1000 r.p.m. The toothed pulley 22, which is fixed to the countershaft 23, rotates about the axis of rotation of the drive shaft 17 and, because of its connection, via the toothed belt 21, to the toothed pulley 19 fixed to the housing of the drive motor, causes the countershaft 23 to rotate within the bowl bearings 24-26. As a result of this movement of the countershaft 23, the gear 27 drives the gear 38 at an angular velocity of $2\omega$ because of the 1:1 gear ratio. As a result, the bowl 40, which like the gear 38 is fixed connected to the hollow shaft 34, rotates at an angular velocity of $2\omega$.

At the same time, the toothed pulley 28, rotating with the countershaft 23, drives the toothed belt 33 which, in turn, drives the toothed pulley 32 fixed to the hollow shaft 29. This causes the hollow shaft 29 to rotate about its own axis at an angular velocity of $-\omega$. As a consequence of this, the bundle 54 of the flexible tubes 55-57 does not become twisted and yet allows fluid communication into and out from the transparent silicon rubber bag 43, without the presence of any rotating seals, When properly balanced, the flow-through centrifuge bowl can be operated at speeds up to 2,000 r.p.m. for the purpose of separating blood components and at even higher speeds for other purposes.

In order to demonstrate the capacity of a flow-through centrifuge according to the invention, heparinized (1.5 mg/kg) sheep blood was introduced into the centrifuge directly from the animal (weight 34 kg) while effluents of plasma and red blood cells were returned (after sampling) to the animal. The flow rates through the individual lines were controlled by two roller pumps, one set on the whole blood line and the other on the plasma return line, the third line having a flow equal to the difference between the two pumps. With a constant feed rate of 60 ml/min, plasma free of red blood cells was harvested at 12 ml/min at 1000 rev/min or 18 ml/min at 1300 rev/min. During 12 hours of continuous flow of plasma at 18 ml/min, blood and plasma samples were collected at intervals so that changes in the platelet counts could be studied. The results shows a 50% reduction in the blood platelet count within the first hour, and a reduction to 30% of the base line values by the twelfth hour of operation without any evidence of red blood cell hemolysis.

It is to be appreciated that the centrifuge bowl 40 (FIGS. 1 and 2) may be replaced or modified, depending on the particular centrifuging task at hand, without departing from the present invention.

Figure 3:
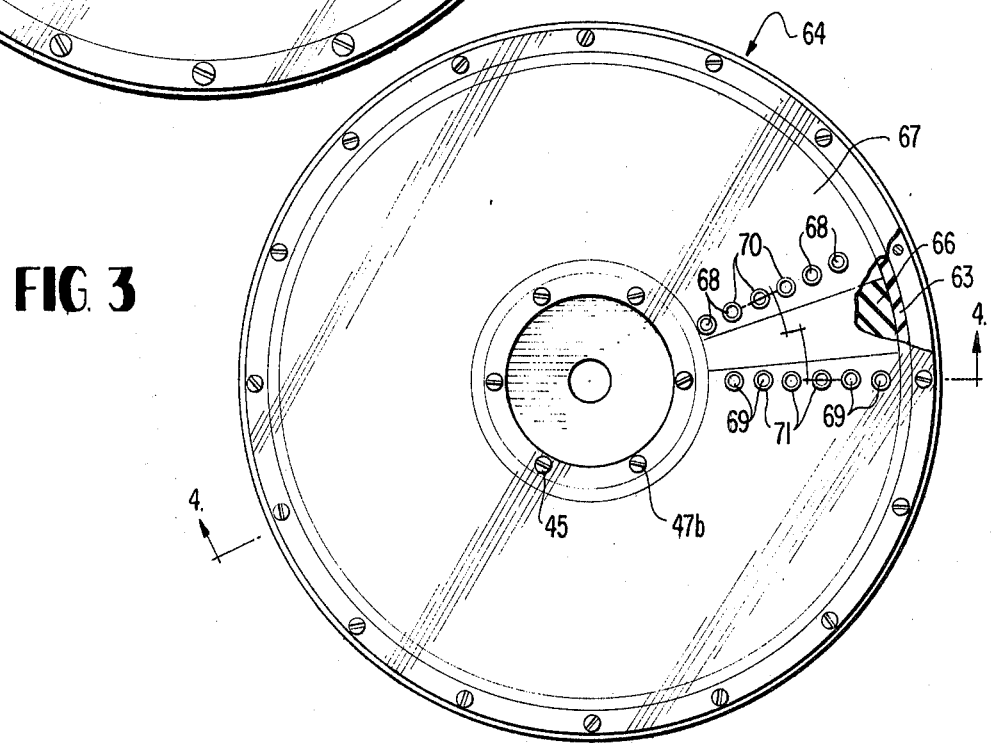
FIG. 3 is a top plan view of a second centrifuge bowl, with an associated plurality of inflow and outflow lines, which can replace the bowl forming part of the centrifuge of FIG. 1 to provide for continuous gradient separation.

In the event it is desired to prove a flow-through centrifuge for effecting continuous density gradient cell separation, it is only necessary to remove the transparent, plastic lid 46 and the transparent, silicon rubber bag 43 from the centrifuge bowl 40 shown in FIGS. 1 and 2. A thin polytetrofluoroethylene sheet 62 is positioned in the bottom of the recess in the base member 41 from which the silicon rubber bag 43 was removed. An outer silicon rubber O-ring 63 or a similar sealing washer, which may be made of silicon rubber or the like, is positioned on top of the sheet 62 adjacent the shoulder 44 for the purpose of sealing the outer periphery of the chamber in which cell separation is to be carried out in the thus modified centrifuge bowl designated generally by the numeral 64. An inner silicon rubber O-ring 65 or a similar sealing washer is positioned on top of the sheet 62 adjacent the shoulder 45 to provide for sealing of the inner periphery of the chamber in which the cell separation is to be carried out. A septum 66 (FIG. 3) made of silicon rubber or the like extends radially outwardly between the inner O-ring 65 and the outer O-ring 63 to provide for radial separation within the chamber in which cell separation is to take place.

A transparent, plastic lid 67, which may be of lucite, of special construction is positioned on the shoulders 44 and 45, defining between its lower surface and the thin sheet 62 a centrifuge chamber. The lid 67 is held in position by the bolts 47a and 47b as in the embodiment illustrated in FIGS. 1 and 2.

Six inlet bores 68 are provided through the lid 67 on that side of the septum 66 which is in the direction of rotation of the centrifuge bowl 64. Six outlet bores 69 are provided through the lid 67 on the other side of the septum 66, as can best be seed in FIG. 3. The bores 68 and 69 allow fluid communication with the centrifuge chamber defined in the space between the inner surface of the transparent lid 67 and the sheet 62. Each of the inlet bores 68 terminate, not in the flat upper surface of the lid 67, but extend through nipple-like protrusions 70 which are particularly adapted to receiving the free ends of flexible tubes which are not unlike the tubes 55–57 shown in FIG. 1. Similarly, each of the outlet bores 69 extend through nipple-like protrusions 71 which upstand from the upper surface of the lid 67.

As illustrated, the six inlet bores 68 are displaced radially from the axis of rotation of the centrifuge bowl 64, which is determined by the axis of rotation of the drive shaft 17 at differing distance, the distance between adjacent ones of the inlet bores 68 being substantially identical. Similarly, the six outlet bores 69 are positioned at different radial distances from the axis of rotation of the centrifuge bowl 64, adjacent ones of the outlet bores 69 being substantially equidistant from one another. The outlet bores 69 as a group are positioned at greater radial distances than the corresponding inlet bores 68, each outlet bore 69 being positioned further radially outward from the axis of rotation of the bowl 64 than its corresponding one of the inlet bores 68.

Each of the inlet bores 68 and each of the outlet bores 69 is to be placed in fluid communication with a respective one of a total of twelve flexible, flow tubes (not illustrated) which are bundled, protected by a tubing preferably filled with silicon grease and led to the outside of the centrifuge via the hollow shaft 34 and the hollow shaft 29 in the same manner as the tubes 55–57, illustrated in FIG. 1.

Figure 4:
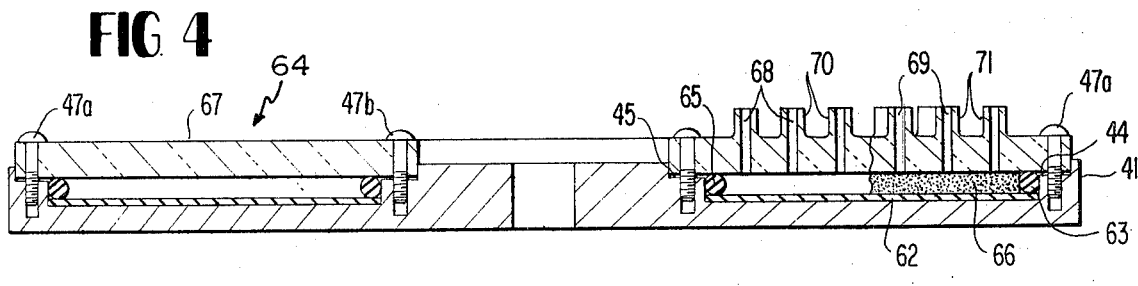
FIG. 4 is a cross-sectional view of the centrifuge bowl of FIG. 3, the section being taken along section line 4—4.

The six inlet feed tubes, in operation, continuously introduce liquids of different density increasing in order from inner to the outer positions of the inlet bores 68, thus creating a density gradient inside the centrifuge bowl 64 within the chamber defined between the inner surface of the lid 67 and the thin sheet 62. Cells suspended in the liquid fed from the innermost hole travel in a spiral path acting under the centrifugal force field resulting in the separation of the cells according to density. The thusly separated cells are continuously eluded through the outlet bores 69 into six fractions. It is to be appreciated, of course, that any number of fractions could be realized, depending principally on the number of inlet and outlet bores and associated tubes provided. It is also to be understood that while cell separation has been particularly mentioned above, the particular centrifuge bowl 64 illustrated in FIGS. 3 and 4 could be used to provide separation of materials other than cells into various fractions according to density.

Figure 5:
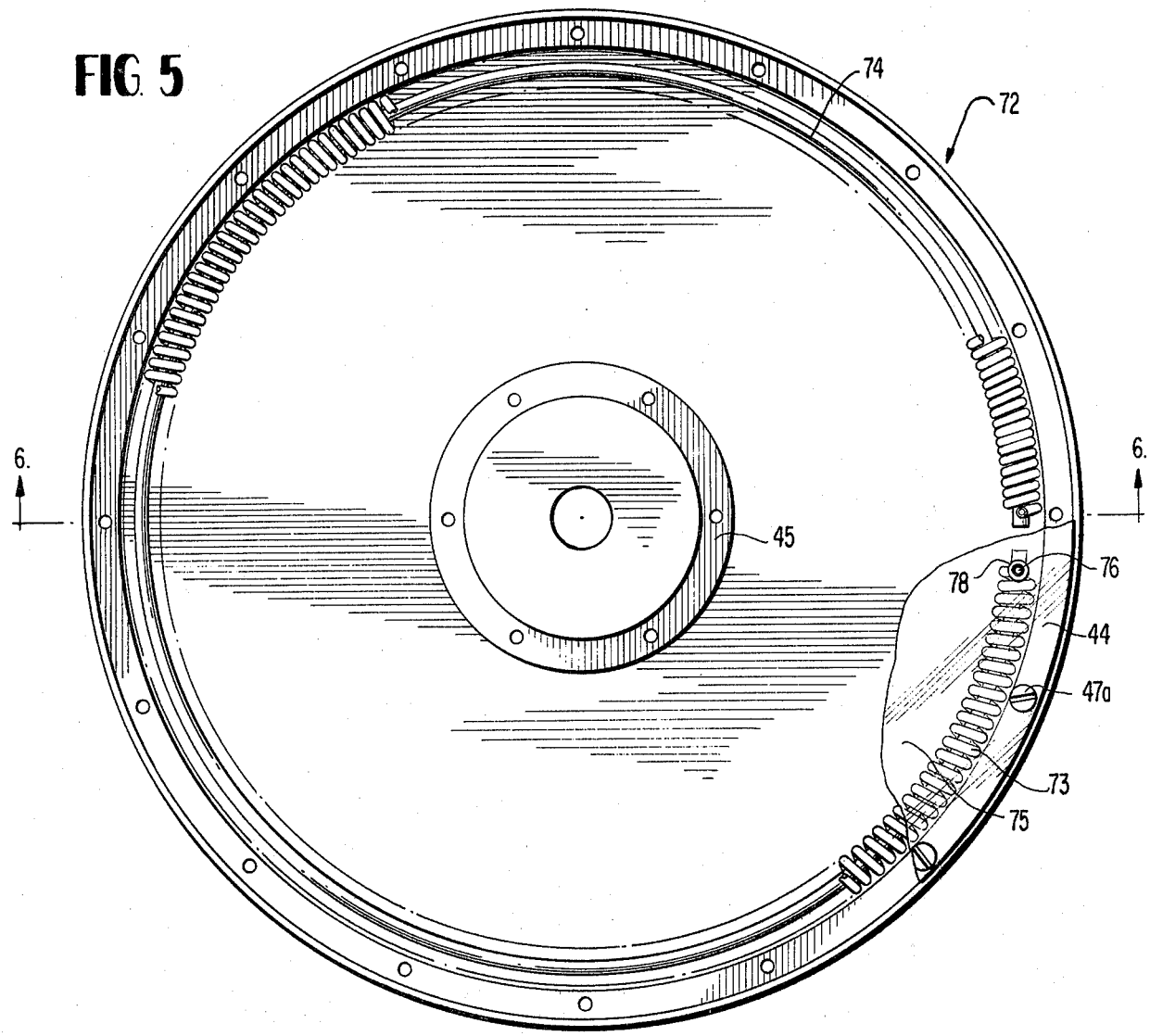
FIG. 5 is a top plan view of a third centrifuge bowl, with an associated inflow line and an outflow line, which can replace the bowl forming part of the centrifuge of FIG. 1 to provide for separation of the mobile phase from the stationary phase of a two-phase solvent system.
Figure 6:
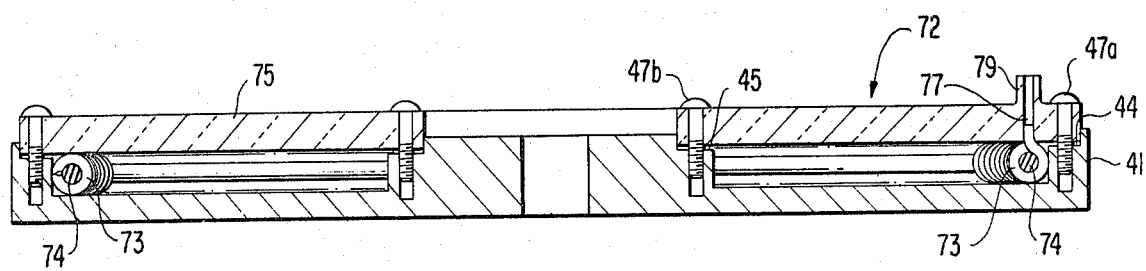
FIG. 6 is a cross-sectional view of the centrifuge bowl of FIG. 5, the section being taken along section line 6—6.

In the event it is desired to adapt the centrifuge of FIG. 1 for use in separating a mobile phase from a stationary phase of a two-phase solvent system or to adapt it to a single system in which particles are to be subjected to eluderation using a single solvent system, it is only necessary to remove the transparent plastic lid 46 and the silicon rubber bag 43 as first steps in providing a modified centrifuge bowl denominated generally by the numeral 72 in FIGS. 5 and 6. A long helix of narrow-bore tubing 73 having two free ends is positioned within the recess defined in the base member 41 adjacent the shoulder 44. Although not necessary, the narrow bore tubing 73 is desirably positioned about a ring 74 of circular cross section, the ring 74 being positioned within the recess in the base member 41 in the vicinity of shoulder 44. Although only one loop of the helically wound narrow-bore tubing 73 is illustrated in FIGS. 5 and 6, it is to be understood that several loops may be made about the recess within the base member 41. A transparent, plastic lid 75, which may be of lucite, is positioned on the shoulders 44 and 45 of the base member 41. As illustrated, the two ends of the tubing 73 are placed in fluid communication with respective bores 76 and 77 which extend through the lid 75 in the vicinity of its outer circumference. The bores 76 and 77 terminate at their upper end not at the flat surface of the lid 75 but, rather the bores 76 and 77 extend through nipple-like protrusions 78 and 79 which extend upwardly from the flat surface of the lid 75, which nipple-like protrusions 78 and 79 allow a flexible inlet tube and a flexible outlet tube to be placed in fluid communication respectively with the bores 76 and 77. Such inlet and outlet tubes (not shown) correspond to the tube 55 and the tube 57 shown in FIG. 1. The free ends of the helically wound narrow-bore tubing 74 are placed in fluid communication with the respective bores 76 and 77 with the aid of nipple-like protrusions on the underside surface of the lid 75, these protrusions being constructed similarly to the nipple-like protrusions 76 and 79. It is to be understood that in some applications, the free ends of the narrow-bore tubing could extend upwardly through somewhat enlarged openings positioned as are the bores 76 and 77 in the lid 75 and be placed in communication with respective inlet and outlet tubes. As in the case of the other embodiments, the inlet and outlet tubes are threaded downwardly through the hollow shaft 34, outwardly to the hollow shaft 29, inwardly to the opening in the fixed member 58 and thence respectively to a supply and to a member which is to receive material eluted through the helix of narrow-bore tubing 73.

Under proper centrifugal force fields, each turn of the helix of narrow-bore tubing 73 retains the stationary phase of a two-phase solvent system, while the mobile phase continuously elutes through it. Thus, a sample solution containing solutes or particles is subjected to a partition process between the two phases and is finally eluted through the outlet tube. In the event a single solvent system is established, particles are subjected to elutriation in each coil of the helix and separated according to size and density under the influence of a centrifugal force field.

It is to be appreciated that flow-through centrifuges made in accordance with the present invention have broad application. Such centrifuges may be applied to plasmopheresis, cell washing and elutriation, zonal centrifugation, and counter-current chromotography, to specifically mention a few of the applications.

The foregoing description and accompanying figures of drawings relate to illustrative embodiments of flow-through centrifuges constructed in accordance with the present invention. These illustrative embodiments have been set out by way of example, not by way of limitation. Other embodiments and numerous variants are possible within the spirit and scope of the present invention, its scope being defined by the appended claims.

What is claimed is:

1. A flow-through centrifuge having a central axis of rotation and comprising a centrifuge bowl rotatable about said central axis; at least one inlet tube and at least one flexible outlet tube, one end of each of said tubes being connected to said bowl and being rotatable therewith for providing fluid communication therewith; a bundle forming a partial loop and composed of said tubes extending radially outwardly from the vicinity of said central axis, along a path radially displaced from said central axis and thence to a point along said central axis; means for nonrotatably securing said tubes constituting said bundle at said point; and means for simultaneously rotating said bundle about said central axis at a velocity of $\omega$, said bowl about said central axis at a velocity of $2\omega$ and said bundle about its own axis at a velocity of $-\omega$, whereby the centrifuge can operate free of rotating seals and without twisting the inlet and outlet tubes.

2. A flow-through centrifuge according to claim 1, wherein said at least one outlet tube comprises two outlet tubes, each of said outlet tubes being connected at one of its ends to said bowl at different radial distances from the central axis.

3. A flow-through centrifuge according to claim 2, wherein said at least one inlet tube is a single inlet tube.

4. A flow-through centrifuge according to claim 1, wherein said at least one inlet tube includes more than two inlet tubes, said inlet tubes being connected at one of their respective ends to said bowl at differing radial distances from the central axis.

5. A flow-through centrifuge according to claim 4, wherein said at least one outlet tube includes a plurality of outlet tubes, said outlet tubes being connected at one of their respective ends to said bowl at differing radial distances from the central axis.

6. A flow-through centrifuge according to claim 4, including a septum means extending radially within said bowl for preventing fluid communication between said inlet and outlet tubes within said bowl except over angular distances approaching 360°.

7. A flow-through centrifuge according to claim 4, wherein said at least one outlet tube includes a plurality of outlet tubes, said outlet tubes being connected at one of their respective ends to said bowl at differing radial distances from the central axis.

8. A flow-through centrifuge according to claim 1, wherein said at least one inlet tube and at least one outlet tube are constituted respectively by one inlet tube and by one outlet tube, and wherein a helically wound tube is supported within said bowl, said helically wound tube having a first end in fluid communication with said one inlet tube and a second end in fluid communication with said one outlet tube.

9. A flow-through centrifuge according to claim 8, wherein said helically wound tube is wound about a circular rod positioned within said bowl.

10. A flow-through centrifuge according to claim 1, including a framework, a hollow shaft positioned centrally, having an axis of rotation coaxial with said central axis and being rotatably carried by said framework; and wherein said means for rotating includes drive means connected to framework for driving said framework at said angular velocity of $\omega$; a countershaft positioned parallel to and radially displaced from said central axis, said countershaft extending through said framework and rotatably supported therein, said countershaft carrying a driven pulley; a drive pulley and a first gear; a second gear meshed with said first gear, said second gear being fixedly connected to said hollow shaft; a fixed pulley positioned on the central axis and stationary with respect to said drive means, said driven pulley being coupled to said fixed pulley for driving said bowl at said angular velocity of $2\omega$ via said countershaft and said first and second gears; a further hollow shaft extending through at least a portion of said framework radially outwardly from said central axis and supported for rotation with respect to its own axis; and a further pulley fixed to said further hollow shaft, said further pulley being coupled to said drive pulley carried on said countershaft for driving said further hollow shaft about its own axis of rotation at said angular velocity of $-\omega$.

11. A flow-through centrifuge according to claim 10, wherein said bundle of said inlet tubes and said outlet tubes is fixed within said further hollow tube for rotation therewith.

12. A flow-through centrifuge in accordance with claim 1, wherein said bowl has an annular shape with said tubes passing through a central opening in said bowl along said central axis in the form of said bundle.

13. A flow-through centrifuge having a stationary motor housing and a central axis of rotation and comprising a centrifuge bowl supported above said housing rotatable about said central axis; at least one inlet tube and at least one flexible outlet tube, one end of each of said tubes being connected to said bowl and being rotatable therewith for providing fluid communication therewith; a bundle forming a partial loop and composed of said tubes extending radially outwardly from the vicinity of said central axis beneath said bowl and above said housing, along a path radially displaced from said central axis, and thence to a point along said central axis above said bowl; means for nonrotatably securing said tubes constituting said bundle at said point; and means for simultaneously rotating said bundle about said central axis at a velocity of w, and said bowl about said central axis at a velocity of 2w.

* * * * *

UNITED STATES PATENT AND TRADEMARK OFFICE
CERTIFICATE OF CORRECTION

PATENT NO. : 4,425,112
DATED : January 10, 1984
INVENTOR(S) : Yoichiro Ito

It is certified that error appears in the above-identified patent and that said Letters Patent are hereby corrected as shown below:

Column 3, line 61, change "slaft" to --shaft--;

Column 4, line 20, change "bowl" to --ball--;

Column 4, line 68, change "polytetrofluoroethylene" to --polytetrafluoroethylene--;

Column 6, line 2, change "thusly" to --thus--;

Column 6, line 3, change "eluded" to --eluted--;

Column 6, line 16, change "eluderation" to --elutriation--;

Column 7, line 9, change "chromotography" to --chromatography--;

Column 8, line 62, change "w" to --$\omega$--;

Column 8, line 63, change "2w" to --$2\omega$--.

Signed and Sealed this

Eighteenth Day of June 1985

[SEAL]

Attest:

DONALD J. QUIGG

Attesting Officer     Acting Commissioner of Patents and Trademarks